United States Patent [19]

Baden

[11] Patent Number: 5,314,699
[45] Date of Patent: May 24, 1994

[54] METHOD FOR FLEA AND INSECT CONTROL

[76] Inventor: Jeffrey Baden, 452 Page Ave., NE., Atlanta, Ga. 30307

[21] Appl. No.: 843,586

[22] Filed: Feb. 28, 1992

Related U.S. Application Data

[63] Continuation of Ser. No. 471,829, Jan. 29, 1990, abandoned.

[51] Int. Cl.⁵ ............................................. A01N 59/14
[52] U.S. Cl. ........................... 424/660; 424/DIG. 10
[58] Field of Search ............... 424/DIG. 10, 657, 658, 424/659, 660; 514/507, 956

[56] References Cited

U.S. PATENT DOCUMENTS

| | | | |
|---|---|---|---|
| 4,363,798 | 12/1982 | D'Orazio | 424/657 |
| 4,374,853 | 2/1983 | Workman | 514/506 |
| 4,438,090 | 3/1984 | Brite | 424/659 |
| 4,461,758 | 7/1984 | Brite | 424/659 |
| 4,610,881 | 9/1986 | Beehgaard | 424/657 |
| 4,617,188 | 10/1986 | Page et al. | 424/658 |
| 4,804,683 | 2/1989 | Steltenkamp | 514/613 |
| 4,826,682 | 5/1989 | Sakharova | 424/659 |
| 4,873,084 | 10/1989 | Sallay | 424/658 |

*Primary Examiner*—Marianne M. Cintins
*Assistant Examiner*—K. Weddington
*Attorney, Agent, or Firm*—Hopkins & Thomas

[57] ABSTRACT

A composition and method for controlling fleas and flea larvae in substrate such as carpeting is disclosed in which a solution and a boron-containing compound are impregnated into the substrate and then extracted, leaving a crystalline boron residue which contaminates the food supply of the insects and abrades the insects' exoskeleton for causing desiccation.

6 Claims, No Drawings

METHOD FOR FLEA AND INSECT CONTROL

This application is a continuation of co-pending application Ser. No. 07/471,829, filed Jan. 29, 1990 now abandoned.

BACKGROUND OF THE INVENTION

Numerous compositions and methods for flea control have been developed and tried. Since fleas are an annoying and potentially health threatening pest, the variety of compositions and methods are widely used. Flea populations are much higher in households with pets than they are out of doors. One major reason for this is that carpets provide an ideal breeding ground with controlled temperatures, no predators, and ample food sources. The cycle of flea evolution begins when flea eggs fall off the host animal into the carpet, the animal's bedding, or on the ground. The egg then hatches and emerges as a larva (worm). The larva has three growth periods or instar stages before it changes into an adult, blood-eating insect. It then moves back to the host animal, and the cycle starts over. As long as the carpets, etc. remain untreated, fleas remain a significant problem for home owners. Fleas are extremely hardy pests, and the larvae can survive for significant periods of time on very little food. In addition, since fleas are extremely productive breeders, once established, the flea population can be extremely large and exhibit an essentially continuous development cycle.

Thus, in treating flea infestations, the treatment, composition, or method must exhibit not only an immediate, but a residual effectiveness to be successful. Powerful insecticides which exhibit such residual effectiveness are available, however, their application in a household environment is unacceptable in many cases. In addition, conventional insecticides are increasingly coming under attack for their toxic effects as a result of their tendency to accumulate in organs and tissues of mammals and their adverse effect on the environment. Thus, there exists a need in the art for an insecticidal composition and method of application which exhibits no deleterious effects on either humans, animals or the environment and which exhibits a residual effectiveness to control the developing larvae.

Boron containing compounds have been utilized for many years, either alone or in combination with other compounds in insecticidal formulations. Some examples of insecticides which employ boron containing compounds are shown by U.S. Pat. No. 4,759,930 to Granirer, et al. for an insect killing composition: U.S. Pat. No. 4,617,188 to Page, et al. for natural insecticides employing borax and carob; U.S. Pat. No. 4,430,090 to Brite for a method of preparing an insecticide containing boric acid; and U.S. Pat. No. 490,688 to Smith for an insecticide. While these references are mainly directed to the control of cockroaches and beetles, it is recognized that boron based products have been utilized for many years as insecticidal compositions.

Steltenkamp, U.S. Pat. No. 4,804,683, describes the effectiveness of his invention, as an insect repellant, of N-lower alkyl neoalkanamides of 1 to 4 carbon atoms in the lower alkyl thereof and of 12 to 14 carbon atoms in the neoalkanoyl group. He gives as examples N-methyl- and N-ethyl neotridecanamides. Steltenkamp describes the various ways that his invention may be applied and the insects against which it is active. He states that the long lasting effectiveness of his invention is "for as long as two weeks."

In each of his examples the active repellents listed are N-methyl neotridecanamide and N-ethyl neotridecanamide. All other ingredients are listed as builders. Steltenkamp further describes the builders as "compositions" that "are employed as means for depositing such active compounds onto surfaces to be made repellent to insects."

Steltenkamp describes his invention as an amide that is used for insect repellency. N-Methyl neotridecanamide which is normally liquid is "sufficiently volatile" and can be detected in the air by insects." Disodium Octaborate Tetrahydrate is a non volatile larvacide that when applied is colorless and odorless. Steltenkamp's teaching is that N-Methyl or N-Ethyl neotridecanamide when broadcast with multiple builders is designed to repel a large variety of insects. Steltenkamp's describes the invention as an insecticide, a killer of the adult specie. In the present invention applications of Disodium Octaborate Tetrahydrate at the rate of 4 to 12 ounces per gallon in an aqueous solution (warm tap water) primarily targets the larva of the targeted pest.

The teaching of Steltenkamp's Patent is that unlike Disodium Octaborate Tetrahydrate, a larvacide, the active ingredients N-Methyl and N-Ethyl neotridecanamide found in his repellant/insecticide acts as an adulticide. Steltenkamp in his teachings does not disclose any of the chemical family Boron as an active ingredient of his invention. Disodium Octaborate Tetrahydrate is an uncommon member of the Boron family.

Workman, U.S. Pat. No 4,374,853 describes his invention as an "insect killing" composition for Ectoparasites, such as fleas that are found on warm blooded animals, i.e. dogs and cats. He further describes his invention as an aqueous antiseptic liquid that contains alcohol and at least one compatible surface active agent. The insect controlling composition is a shampoo containing a high percentage of alcohol, which is the active insecticidal ingredient.

Described in Workman's Patent are "Surface Active Agents and Detergents" that can be found in Volumes 1 and 2 of the literature by Schwartz, Perry and Berch. Workman continues to describe commercially available surfactant components to which his invention adds high amounts of alcohol, preferably ethanol. In his teaching, Workman prescribes the saturation of the animal to be treated with a surfactant/antiseptic solution that contains a 26% to 29% concentration by volume of alcohol. The animal is treated with this solution for up to five minutes and the solution is removed with clean water. Workman's treatment leaves the treated animal free of adult flea infestation. In testing he states that "a gross visual examination two weeks later indicated no fleas or flea residue." Nowhere in his teaching does he describe the long lasting effect of his invention by the introduction of a new adult flea infestation.

Workman's invention does not differ in its application or results from any other known teaching that use similar active ingredients i.e. Pyrethrin, Pyrethroid, Sumethrin, D-Limonene, Royal Penny, Melaleuca Alternifolia, Oil of Cedar, and Rotenone to eliminate flea infestation in warm blooded animals. In each and every invention using these insecticides, the inventor's describe and make a claim that is emulated by Workman. Products that are commercially available under names such as Lamber Kay's—Xenox Flea & Tick Shampoo or Victory Flea & Tick Shampoo, Farnam's—Flea Stop, or Cardinal/De Vos Laboratories—Rid, Flea & Tick Shampoo all recommend the treatment of the premises inhabited by the dog and cat to prevent further flea infestation of the animal. Modern Veterinary Medicine teaches us that there are several categories of flea control products. They are, Pyrethrins (Pyrethroids), Organophosphates, Carbamates, Chlorinated-hydrocarbons, Repellents Botanicals like the citrus based D-Limonene and the derris derived Rotenone. There are also several miscellaneous compounds, like petroleum distillates, insect growth regulators and synergists: i.e. Piperonyl Butoxide. Both Steltenkamp's and Workman's inventions fall into the category of miscellaneous compounds. Each of the inventors employs a petroleum distillate as the active ingredient in their invention.

However, the compositions disclosed in the known prior art and their method of application would not be generally effective for flea control due to factors such as the extremely small size of the flea larvae, the multiplicity of areas in which the flea larvae thrive, and the formulation and application of the insecticidal formulations themselves.

SUMMARY OF THE INVENTION

It is, therefore, one of the principal objects of the present invention to provide a composition and method for flea control which utilizes biodegradable materials, which is easily applied to large surface areas, such as carpets, and which exhibits a high degree of residual effectiveness against flea larvae.

Another object of the present invention is to provide a composition for flea control in which the active ingredient is easily applied to carpets with a spray-type applicator, conventional carpet cleaning equipment, or other suitable means and which has no deleterious effects on either the carpet or on humans or animals utilizing the carpeted areas.

A further object of the present invention is to provide a method for flea control in carpets, which method is relatively inexpensive and which can be easily accomplished by home owners.

These and additional objects are attained by the present invention which relates to a composition and method for flea control which involves the formulation of an insecticidal composition using a boron based compound which is mixed with a liquid such as water, a carpet cleaning solution, or with another suitable carrier. In the method of application, the resulting composition may be applied to carpeting with conventional injection/extraction, hot water carpet cleaners, or it may be sprayed on with other means. The application of the compound is easily accomplished with such equipment and disposes the active ingredient in the carpet backing and throughout the carpet fibers where the flea larvae hatch and mature. The present composition provides contamination of the food sources of the larvae without exhibiting toxicity to humans or animals. More importantly, however, a synergistic effect is exhibited by the present composition which, due to its method of application, has a deleterious abrasive effect on the exoskeleton of the larvae, thus providing residual effectiveness as a larvacide.

Various additional objects and advantages of the present invention will become apparent from the following description.

DETAILED DESCRIPTION OF THE PREFERRED EMBODIMENT

An insecticidal compound is formed using boron or a boron containing compound as its primary ingredient. A preferred compound is disodium octaborate tetrahydrate, being from the chemical family of sodium borate, and having the formula $Na_2B_8O_{13} \cdot 4H_2O$. The compound is a white odorless powder that is relatively inert, non corrosive and easily handled. The boron based chemical occurs naturally as Razorite or Kernite. The Boron is processed and produces an essentially pure natural crystal that is known as Disodium Octaborate Tetrahydrate. It is an all natural crystal that has a physical hazard rating, by the national fire Protection Association, for health, flammability and Reactivity of "0". Disodium Octaborate Tetrahydrate is both biodegradable and non-polluting.

The active ingredient, disodium octaborate tetrahydrate in essentially pure form, is either mixed with a suitable hot water and detergent solution used for shampooing carpets, plain water, or another suitable carrier. The carrier has as its purpose the transport of the boron or boron compound into the substrate whereupon the carrier is removed, evaporates, or is caused to evaporate, leaving a crystalline residue. Other possible compounds or elements include elemental boron, 5 Mol. and 10 Mol. borax, boric acid, boron salts and oxides, and other boron-containing compositions.

Like Steltenkamp's invention, Disodium Octaborate Tetrahydrate has in testing, been proven effective against insects other than the flea that make their home in carpeting and in furniture. Disodium Octaborate Tetrahydrate when applied to carpets and furniture, is active against termites, clothes moths, carpet beetles, cockroaches, mites and fungus.

Unlike Steltenkamp's invention, long term testing has proven that Disodium Octaborate Tetrahydrate in a form that is essentially pure, when applied in aqueous solution or with a carpet cleaning surfactant that are used as builders will, upon evaporating, bind the active ingredient, a crystal, to the backing of the carpet and the base of the fibers. The residual effects are that the crystals will remain active until the carpet is cleaned again.

While relative proportions may vary, in general, one or two cups, comprising four to eight ounces net weight of the boron containing compound, is mixed with one gallon of hot water and detergent solution of the type normally used for cleaning carpeting. The cleaning solution is prepared according to the directions supplied by the equipment manufacturer, and the boron containing compound is then added to the resulting mixture. The carpet cleaning equipment normally utilizes heated water and the mixture is thoroughly impregnated into the carpeting. The solution is injected throughout the fibers of the carpet and the fibrous matting or backing which holds the tufts of carpet by the carpet shampooing equipment. Of the injected composition, approximately fifty to ninety percent (50%-90%) of the liquid solution is extracted by the carpet cleaning equipment depending on the thickness of the pile which leaves a residue in the carpet fibers and the backing. As the water evaporates and the carpet dries, the boron in the solution dries into a crystalline form, normally sodium borate. The method of application of the present composition disposes the majority of the crystals thus formed in the carpet backing, away from any substantial human or animal contact, but in the area of the carpet where a majority of the larvae hatch and begin their life cycle. As an alternative, a solution of water and a boron-containing composition can be sprayed into the carpet and allowed to dry, thus leaving the crystalline boron residue.

The present invention provides two separate and distinct, yet cooperative methods of flea control. The larvae of the flea will feed on virtually anything which contains either proteins, fats, or carbohydrates and includes things such as hair, skin, food crumbs, other flea droppings, etc. Thus, utilizing the present compound and method, the food supply of the larvae is coated with the boron containing composition. Ingestion of the material by the larvae causes the digestive tract of the insect to become clogged, resulting in the death of the larvae.

The second effect of the injection of the boron compound and the residue remaining in the carpet involves the crystallinization of the boron compound as it dries. In its crystalline form, the boron compound exhibits extremely sharp and abrasive edges all around the perimeter of the microscopic crystals. As the eggs hatch and the larvae migrate around the backing and fibers of the carpet, the sharp edges of the crystals abrade the exoskeleton of the larvae, especially at skin folds, and the areas where the appendages of the insect join the body. The abrasion causes desiccation and death from dehydration. It can thus be appreciated that a continuous detrimental effect is exhibited and one which can remain effective for as long as one year.

Since the contamination of the larval food serves as a systemic poison and not a neurotoxin as do many commercial insecticides, there is no build-up of immunity in the pests. In addition, the overall population of fleas is also reduced by reducing a primary source of infestation, that being the carpet or other substrate to which the present composition is applied. In tests conducted on the present composition and method in the laboratory, a larval mortality rate of one hundred percent was exhibited as long as three months after application of the composition with a formula containing four ounces per gallon of solution, while a formulation using eight ounces of the boron compound per gallon of solution exhibited a one hundred percent mortality rate as long as four months after application. The tests were then concluded, however, the effectiveness of the control did not appear to lessen.

The tests are summarized below. It should be noted, however that these tests were actually more difficult than a real-life situation. New carpeting was used, thus eliminating some sources of food which would normally be present and thus reducing the mortality rate from ingestion of the boron-tainted food supply. In addition, only third instar stage larvae were used to seed the carpet. Younger larvae in such an environment are expected to have even greater mortality rates due to their increased contact with the rough crystals and their less highly developed exoskeleton.

Immediate insecticidal effectiveness of the composition was evident from a near one hundred percent mortality rate after one day. In contrast, an untreated control sample exhibited no mortality of the larvae. The method of application used in the present invention ensures that there will be no loose, accessible, or visible product, and the carpet cleaning activity itself removes and kills most adult fleas, if any, present in the carpet. The composition itself is essentially safe for the carpeting, in that the composition will not break down chemicals employed in many of the present generation of stain resistors applied to new carpeting. An important feature of the present invention is the fact that the composition is inaccessible to humans and pets when applied according to the present method, is non-toxic, and provides effective control for months at a time.

It has also been found, in conducting the above-referenced tests, that the present composition is an effective fungicide and mold inhibitor, due to a combination of the sterilization effect of the boron-containing compound and the cleaning effect of the detergent solution of the carpet cleaning machine. It will be appreciated that a novel, safe and effective means of flea and fungus control is provided by the present invention.

TABLE 1

RESULTS

The residual effectiveness of boron in carpet cleaning solution in controlling cat flea larvae in ⅜ in. pile carpet.

| Chemical and Rate | Rep. | Percentage mortality Day and months | | | | |
|---|---|---|---|---|---|---|
| | | 1-Day | 1 | 2 | 3 | 4 |
| Boron 1 cup/gal | 1 | 100 | 100 | 90 | 70 | 60 |
| | 2 | 100 | 90 | 100 | 80 | 50 |
| | 3 | 90 | 100 | 100 | 70 | 70 |
| | 4 | 90 | 100 | 100 | 100 | 80 |
| Boron 2 cup/gal | 1 | 100 | 100 | 100 | 100 | 100 |
| | 2 | 100 | 90 | 100 | 100 | 90 |
| | 3 | 100 | 100 | 100 | 90 | 100 |
| | 4 | 100 | 100 | 90 | 100 | 100 |
| Untreated Control | 1 | 0 | 0 | 10 | 20 | 0 |
| | 2 | 0 | 0 | 10 | 0 | 0 |
| | 3 | 0 | 0 | 0 | 0 | 10 |
| | 4 | 0 | 10 | 0 | 10 | 10 |

Thus, while a composition and a method for flea control and modifications thereof have been described in detail herein, various additional changes and modifications may be made without departing from the scope of the present invention.

I claim:

1. A method for controlling adult insects and larvae in a substrate comprising the steps of:
   preparing a liquid solution for introduction into said substrate;
   adding disodium octaborate tetrahydrate to said solution in the amount of approximately four to eight ounces per gallon;
   impregnating said substrate with said solution; and
   allowing said substrate to dry whereupon a portion of said disodium octaborate tetrahydrate remains in said substrate and dries to a crystalline form for regulating growth by coating the food supply and abrading the exoskeletion of the larvae and insects as they contact said crystalline form of said disodium octaborate tetrahydrate to effect desiccation and thereby death.

2. The method of claim 1 wherein said substrate is a carpet.

3. The method of claim 1 wherein said solution is impregnated into said substrate and extracted therefrom with an injection/extraction spray nozzle of a shampooing device.

4. The method of claim 1 in which said solution is water.

5. The method of claim 1 in which said solution comprises water and a detergent.

6. A method for controlling fleas and flea larvae in carpeting comprising the steps of:

a) preparing a solution comprising a detergent and a liquid carrier for cleaning the carpet utilizing a hot water injection/extraction cleaning appliance;

b) mixing disodium octaborate tetrahydrate with said solution in the amount of approximately four to eight ounces per gallon;

c) injecting the resulting mixture into the carpet such that the solution penetrates through to the backing material;

d) extracting a major portion of said solution, leaving a residual coating of said disodium octaborate tetrahydrate in said carpet and backing material; and e) allowing said residual coating to dry to a crystalline form for contaminating the food sources of the insects and for regulating the growth of the insects by abrading the exoskeletons of the insects which contact said dried coating to effect their death by desiccation.

* * * * *